United States Patent
Li et al.

(10) Patent No.: US 11,286,771 B2
(45) Date of Patent: Mar. 29, 2022

(54) IN-SITU SURFACTANT RETENTION EVALUATION USING SINGLE WELL CHEMICAL TRACER TESTS

(71) Applicant: ConocoPhillips Company, Houston, TX (US)

(72) Inventors: Gaoming Li, Houston, TX (US); Riley B. Needham, Houston, TX (US); Sriram Solairaj, Houston, TX (US)

(73) Assignee: ConocoPhillips Company, Houston, TX (US)

(*) Notice: Subject to any disclaimer, the term of this patent is extended or adjusted under 35 U.S.C. 154(b) by 569 days.

(21) Appl. No.: 16/042,073

(22) Filed: Jul. 23, 2018

(65) Prior Publication Data

US 2019/0032479 A1 Jan. 31, 2019

Related U.S. Application Data

(60) Provisional application No. 62/537,091, filed on Jul. 26, 2017.

(51) Int. Cl.
| | |
|---|---|
| *G01N 33/24* | (2006.01) |
| *E21B 47/11* | (2012.01) |
| *E21B 49/00* | (2006.01) |
| *E21B 49/08* | (2006.01) |
| *E21B 43/16* | (2006.01) |
| *C07B 59/00* | (2006.01) |

(52) U.S. Cl.
CPC .............. *E21B 47/11* (2020.05); *E21B 43/16* (2013.01); *E21B 49/008* (2013.01); *E21B 49/088* (2013.01); *G01N 33/241* (2013.01); *C07B 59/004* (2013.01); *Y10T 436/13* (2015.01)

(58) Field of Classification Search
CPC .... G01N 33/241; E21B 49/088; Y10T 436/13
USPC ...................................... 436/27–29
See application file for complete search history.

(56) References Cited

U.S. PATENT DOCUMENTS

| | | | |
|---|---|---|---|
| 3,623,842 A | 11/1971 | Deans | |
| 3,990,298 A * | 11/1976 | Deans | E21B 47/11 73/152.39 |
| 4,099,565 A * | 7/1978 | Sheely, Jr. | E21B 47/11 166/252.2 |
| 4,168,746 A | 9/1979 | Sheely | |
| 4,273,187 A | 6/1981 | Satter | |
| 4,278,128 A | 7/1981 | Satter | |
| 4,433,727 A * | 2/1984 | Argabright | C09K 8/588 166/252.1 |

(Continued)

FOREIGN PATENT DOCUMENTS

WO  2019023100 A1  1/2019

OTHER PUBLICATIONS

Sheely, C. Q. et al, Journal of Petroleum Technology 1982, 1887-1896.*

(Continued)

*Primary Examiner* — Arlen Soderquist
(74) *Attorney, Agent, or Firm* — Polsinelli PC

(57) ABSTRACT

The present disclosure provides methods for determining surfactant retention values in subterranean reservoirs. In particular, the methods comprise conducting at least one single well chemical tracer test and performing a straight line analysis on a saturation profile of the subterranean reservoir.

16 Claims, 4 Drawing Sheets
(4 of 4 Drawing Sheet(s) Filed in Color)

(56) References Cited

U.S. PATENT DOCUMENTS

| | | | | |
|---|---|---|---|---|
| 4,439,332 | A | * | 3/1984 | Frank .................. C09K 8/58 166/275 |
| 5,212,093 | A | * | 5/1993 | Richardson ............ E21B 49/00 436/27 |
| 5,256,572 | A | * | 10/1993 | Tang .................. E21B 49/005 436/27 |
| 5,905,036 | A | * | 5/1999 | Pope .................... B09C 1/00 435/262 |
| 6,321,595 | B1 | | 11/2001 | Pope |
| 9,410,424 | B2 | | 8/2016 | Agenet |
| 2010/0300682 | A1 | * | 12/2010 | Thakur ................. E21B 43/00 166/250.01 |
| 2014/0034306 | A1 | | 2/2014 | Southwick et al. |

OTHER PUBLICATIONS

O'Brien, G. M, Water-Resources Investigations Report 96-4293, 1997, 41 pages.*

Callegaro, C. et al, International Petroleum Technology Conference 2014, paper IPTC-17951-MS, 15 pages.*

International Search Report and Written Opinion dated Oct. 17, 2018 from related international application No. PCT/US18/43235, 9 pp.

Mikalsen, Numerical Simulation of an Ekofisk Single Well Chemical Tracer Test, NTNU—Trondheim Norwegian University of Science and Technology Petroleum Geoscience and Engineering, Jun. 2014, 133 pp.

Extended Search Report, EP Application No. 18838334.3, dated Mar. 30, 2021.

* cited by examiner

IN-SITU SURFACTANT RETENTION EVALUATION USING SINGLE WELL CHEMICAL TRACER TESTS

CROSS-REFERENCE TO RELATED APPLICATIONS

This application claims priority to U.S. Provisional Application Ser. No. 62/537,091, filed Jul. 26, 2017, the disclosure of which is hereby incorporated by reference in its entirety.

FIELD OF THE INVENTION

The present disclosure relates to methods for determining surfactant retention values in subterranean reservoirs comprising one or more surfactants.

BACKGROUND OF THE INVENTION

Surfactant retention is one of the key parameters for an Enhanced Oil Recovery (EOR) process that involves injection of one or more surfactants into a reservoir. Generally, the surfactant retention is obtained in the lab using a coreflood setup. Due to many factors (i.e., small core sample, reservoir heterogeneity, core aging, etc.), the coreflood surfactant retention value may not be a good representation of the field value. Previous test methods have relied on a small-scale confined inter-well pilot, which can be very costly and time consuming. By obtaining the information from the single well chemical tracer test (SWCTT), the field operations can often skip the small-scale inter-well pilot and go directly to larger scale testing thereby accelerating the EOR project in the exploitation of the field.

What is needed, therefore, is a fast and low-cost method for determining surfactant retention value and residual oil content in a subterranean reservoir.

SUMMARY OF THE INVENTION

One aspect of the present disclosure is directed to a method for determining a surfactant retention value in a subterranean reservoir comprising one or more surfactants. The method comprises (a) generating a saturation profile using at least one single well chemical tracer test, wherein the at least one single well chemical tracer test comprises injecting into the subterranean reservoir at least three chemically reactive tracers; and (b) conducting a straight line analysis to determine the surfactant retention value.

Other aspects and iterations of the disclosure are described in more detail below.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
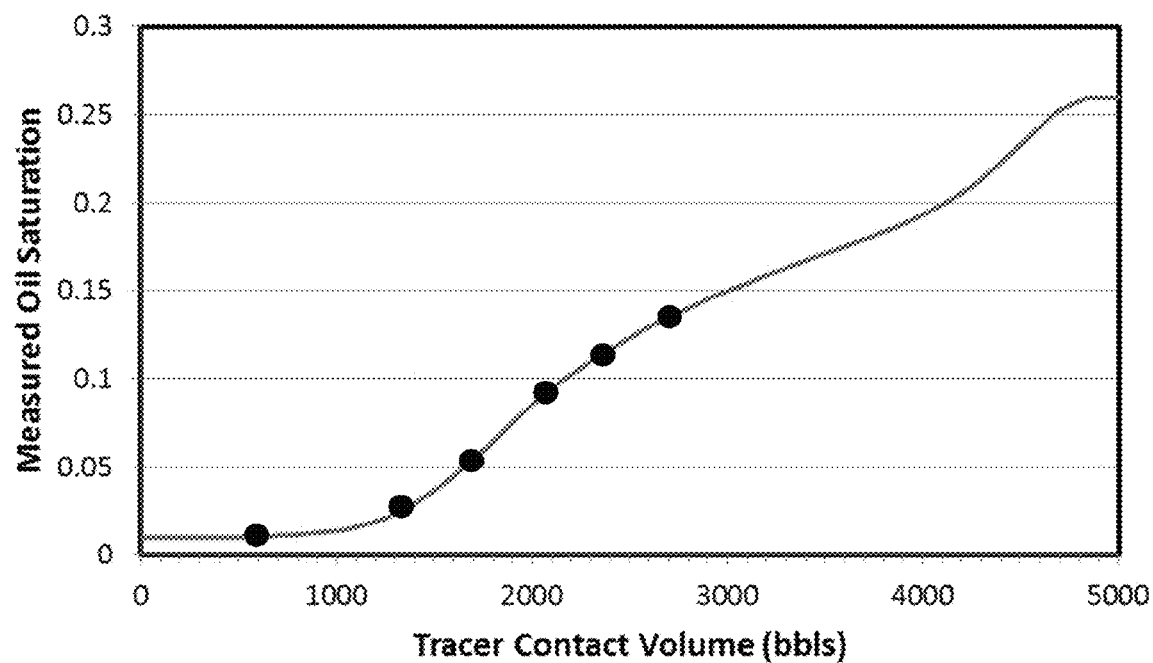
FIG. 1A depicts a graph of measured oil saturation vs. tracer contact volume, in barrels (bbls).

Provided herein are methods for determining surfactant retention values in a subterranean reservoir comprising one or more surfactants. The methods comprise conducting at least one single well chemical tracer test to determine a saturation profile of the subterranean reservoir. The at least one single well chemical tracer test disclosed herein may comprise injecting into the subterranean reservoir at least three chemically reactive tracer. In particular, the at least one chemical reactive tracer test provides more data points on a saturation profile to yield a more quantitative surfactant retention value of the subterranean reservoir. In a preferred embodiment, the methods described herein utilize two single well chemical tracer tests. The first single well chemical tracer test comprises injecting at least three chemically reactive tracers in a first volume into the subterranean reservoir and a second single well chemical tracer test comprises injecting at least three chemically reactive tracers in a second volume into the subterranean reservoir.

(I) Method of Measuring Surfactant Retention Value or Residual Oil Content

One aspect of the present disclosure encompasses measuring a surfactant retention value or a residual oil content of a subterranean reservoir comprising one or more surfactants.

(a) Subterranean Reservoir Comprising Surfactant(s)

In general, the subterranean reservoir comprises at least one surfactant. In an embodiment, the at least one surfactant may be injected into the subterranean reservoir as part of an EOR method.

(i) Surfactant Identity

Suitable surfactants include, without limit, anionic surfactants, cationic surfactants, and nonionic surfactants. Anionic surfactants include, without limit, alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Cationic surfactants include, without limit, alkyl trimethyl quaternary ammonium salts, alkyl dimethyl benzyl quaternary ammonium salts, dialkyl dimethyl quaternary ammonium salts, and imidazolinium salts. Nonionic surfactants, without limit, include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkyl polyethylene glycol esters and diesters. Also included are betaines and sultanes, amphoteric surfactants such as alkyl amphoacetates and amphodiacetates, alkyl amphopropripionates and amphodipropionates, and alkyliminodiproprionate.

The surfactant(s) may be a quaternary ammonium compound, an amine oxide, an ionic or nonionic surfactant, or any combination thereof. Suitable quaternary amine compounds include, without limit, alkyl benzyl ammonium chloride, benzyl cocoalkyl($C_{12}$-$C_{18}$)dimethylammonium chloride, dicocoalkyl ($C_{12}$-$C_{18}$)dimethylammonium chloride, ditallow dimethylammonium chloride, di(hydrogenated tallow alkyl)dimethyl quaternary ammonium methyl chloride, methyl bis(2-hydroxyethyl cocoalkyl($C_{12}$-$C_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, and hydrogenated tallow alkyl (2-ethylhexyl) dimethyl quaternary ammonium methyl sulfate The surfactant(s) may be part of a polymer composition. Polymer compositions may comprise, without limit alkali-surfactant polymer (ASP) composition, surfactant polymer (SP) composition, and alkali-polymer (AP) composition. Suitable ASP and AP compositions comprise an alkali metal and a polymer. Suitable alkali metals include Group IA metals. Suitable polymers include, without limit, polyacrylamides, partially hydrolyzed polyacrylamides, polyacrylates, ethylenic co-polymers, biopolymers, carboxymethylcelloluses, polyvinyl alcohols, polystyrene sulfonates, polyvinylpyrrolidones, and 2-acrylamide-methyl propane sulfonate (AMPS). Suitable surfactant polymer (SP) compositions include, without limit, polyacrylamides, partially hydrolyzed polyacrylamides, polyacrylates, ethylenic co-polymers, biopolymers, carboxymethylcelloluses, polyvinyl alcohols, polystyrene sulfonates, polyvinylpyrrolidones, and 2-acrylamide-methyl propane sulfonate (AMPS).

(ii) Injection

In general, the one or more surfactants may be injected into the subterranean reservoir through an injection well. The rate of surfactant injected into the subterranean reservoir is generally not critical and can and will vary depending on the properties of the subterranean formation (e.g., reservoir temperature and salinity, size, geology, etc.). Such rate can be determined by one of skill in the art. The amount of surfactant(s) injected into the subterranean reservoir can and will vary depending on the properties of the subterranean formation (e.g., reservoir temperature and salinity, size, geology, etc.). Such amount can be determined by one of skill in the art.

(iii) Subterranean Reservoir Properties

In an embodiment, the salinity of the subterranean reservoir may be from about 10,000 ppm to about 250,000 ppm. In some embodiments, the salinity of the subterranean reservoir may be about 10,000 ppm, about 15,000 ppm, about 20,000 ppm, about 25,000 ppm, about 30,000 ppm, about 35,000 ppm, about 40,000, about 45,000 ppm, about 50,000 ppm, about 55,000 ppm, about 60,000 ppm, about 65,000 ppm, about 70,000 ppm, about 75,000 ppm, about 80,000 ppm, about 85,000 ppm, about 90,000 ppm, about 95,000 ppm, about 100,000 ppm, about 105,000 ppm, about 110,000 ppm, about 115,000 ppm, about 120,000 ppm, about 125,000 ppm, about 130,000 ppm, about 135,000 ppm, about 140,000 ppm, about 145,000 ppm, about 150,000 ppm, about 155,000 ppm, about 160,000 ppm, about 165,000 ppm, about 170,000 ppm, about 175,000 ppm, about 180,000 ppm, about 185,000 ppm, about 190,000 ppm, about 195,000 ppm, about 200,000 ppm, about 205,000 ppm, about 210,000 ppm, about 215,000 ppm, about 220,000 ppm, about 225,000 ppm, about 230,000 ppm, about 235,000 ppm, about 240,000 ppm, about 245,000 ppm, or about 250,000 ppm.

In an embodiment, the temperature of the subterranean reservoir may be from about 4° C. to about 120° C. In some embodiments, the temperature of the subterranean reservoir may be about 4° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

(b) Using a Single-Well Chemical Tracer Test to Generate a Saturation Profile

Another aspect of the present disclosure encompasses conducting at least one single well chemical tracer test (SWCTT). SWCTTs are generally known and used in the art to assess residual oil saturation or remaining oil saturation in subterranean reservoirs. SWCTT comprise injecting into a subterranean reservoir at least three chemically reactive tracers, shutting-in the well to allow the at least three chemically reactive tracers to react, and sampling a produced fluid to determine the concentration of at least three unreacted chemically reactive tracers and the corresponding product tracers. The concentration of each chemically reactive tracer and its product tracer can be plotted against a produced fluid volume to generate a residual oil saturation. The residual oil saturations can then be used to generate a saturation profile for the subterranean reservoir.

Each of the components and properties of the SWCTT and the saturation profile are detailed below.

(i) Chemically Reactive Tracer

In general, the SWCTT comprises injecting into a subterranean reservoir at least one chemically reactive tracer. In some embodiments, the SWCTT comprises injected into a subterranean reservoir one chemically reactive tracer, two chemically reactive tracers, three chemically reactive tracers, four chemically reactive tracers, five chemically reactive tracers, or six chemically reactive tracers. In preferred embodiments, the SWCTT comprises injecting into a subterranean reservoir at least three chemically reactive tracers.

In general, the chemically reactive tracer comprises substances such as an ester which partly hydrolyze to form an alcohol (i.e., product tracer) and a an acid when they are contacted with water in a subterranean reservoir. The identity of the chemically reactive tracer can and will vary depending on, for example, the properties of the subterranean formation (e.g., reservoir temperature and salinity). For example, formate esters hydrolyze approximately 50 times faster than acetate esters. Additionally, formate esters can be used in subterranean reservoirs having a temperature of from about 21° C. to about 60° C., and slower-reacting acetate esters can be used in subterranean reservoirs having a temperature of from about 60° C. to about 120° C. The identity of the chemically reactive tracers can be determined by one skilled in the art. Suitable chemically reactive tracers include, without limit, methyl acetate, ethyl acetate, propyl acetate, isopropyl acetate, t-butyl acetate, ethyl acetoacetate, ethyl acrolate, ethyl methacrolate, ethyl butylate, ethyl benzoate, methyl formate, ethyl formate, propyl formate, isobutyl formate, t-butyl formate, dimethyl maleate, dimethyl fumarate, dimethyl phthalate, dimethyl glutarate, dimethyl succinate, methyl salicylate, methyl methacrylate, methyl acrylate, isobutyl methacrylate, isobutyl acrylate, ethylene glycol monomethyl ether acetate, ethylene glycol monethyl ether acetate, ethylene glycol monobutyl ether acetate, ethyl oxalate, ethyl methacrylate, ethyl butylate, or ethyl acrylate. In some embodiments, the chemically reactive tracer may be methyl acetate, ethyl acetate, isopropyl acetate, t-butyl acetate, propyl formate, or ethyl formate.

(ii) Injection

In an embodiment, the at least three chemically reactive tracers may be injected into the subterranean formation via an aqueous composition. The aqueous composition may comprise, without limit, produced water, purified water, recycled water from a produced water stream, or a brine solution. In some embodiments, the aqueous composition is a brine solution. In an embodiment, the aqueous composition may comprise a brine solution having a salinity equivalent to the salinity of the formation brine. The salinity of the formation can be determined by one of skill in the art. The salinity at which the aqueous composition may be injected into the subterranean reservoir can be determined by one of skill in the art.

In an embodiment, the at least three chemically reactive tracers injected into the subterranean reservoir may be allowed to travel through the subterranean reservoir thereby allowing natural gradients to carry the at least three chemically reactive tracers further into the subterranean reservoir. In some embodiments, the at least three chemically reactive tracers are injected into the subterranean reservoir by pumping. Pumping may be accomplished using methods and equipment well known to those skilled in the art. In an embodiment, the at least three chemically reactive tracers are injected into the subterranean reservoir and then an amount of brine without any chemically reactive tracers is injected into the subterranean reservoir.

The at least three chemically reactive tracers may be injected into the subterranean reservoir one at a time as a single slug, simultaneously, sequentially, intermittently, or continuously over a period of time. In preferred embodiments, the at least three chemically reactive tracers may be injected into the subterranean reservoir all at once as a single slug. In still a preferred embodiment, the at least three chemically reactive tracer may be injected into the subterranean reservoir one after another. In yet another embodiment, the tracers may be injected sequentially based on one or more physical properties, such as molecular weight, diffusivity, or retention.

The rate of injecting the at least three chemically reactive tracers into the subterranean reservoir is generally not critical and can and will vary depending on the properties of the subterranean formation (e.g., reservoir temperature and salinity, size, geology, etc.). Such rate can be determined by one of skill in the art.

In an embodiment, the methods disclosed herein comprise at least one single well chemical tracer test. In some embodiments, the methods disclosed herein comprise one single well chemical tracer test, two single well chemical tracer tests, three single well chemical tracer tests, four single well chemical tracer tests, five single well chemical tracer tests, or six single well chemical tracer tests. In a preferred embodiment, the methods disclosed herein comprise two single well chemical tracer tests. In other embodiments, the methods disclosed herein comprise two single well chemical tracer tests, the first single well chemical tracer test comprises injecting at least three chemically reactive tracers one after the other in a first volume and the second single well chemical tracer test comprising injecting at least three chemically reactive tracers one after the other in a second volume. In some embodiments, the ratio of the first volume to the second volume may be from 1:1 to 1:5. In other embodiments, the ratio of the first volume to the second volume may be 1:1, 1:1.5, 1:2, 1:2.5, 1:3, 1:3.5, 1:4, 1:4.5, or 1:5.

In general, the aqueous composition may be injected into the subterranean reservoir at or near the temperature of the subterranean reservoir. The temperature at which the aqueous composition may be injected into the subterranean reservoir can be determined by one of skill in the art.

The amount of at least three chemically reactive tracers injected into the subterranean formation can and will vary depending on, for example, the identity of the aqueous composition and the properties of the subterranean formation (e.g., reservoir temperature and salinity, size, geology, etc.). The amount of the at least three chemically reactive tracers will be an amount sufficient such that all the at least three chemically reactive tracers introduced are in amounts which can be detected at a sampling point(s) after the at least three chemically reactive tracers will travel a given distance through the subterranean formation.

In some examples, the amount of the at least three chemically reactive tracers present in the aqueous composition may be from about 0.1 wt. % to about 10 wt. %. In other embodiments, the amount of at least three chemically reactive tracers present in the aqueous composition may be about 0.1 wt. %, about 0.5 wt. %, about 1.0 wt. %, about 1.5 wt. %, about 2.0 wt. %, about 2.5 wt. %, about 3.0 wt. %, about 3.5 wt. %, about 4.0 wt. %, about 4.5 wt. %, about 5.0 wt. %, about 5.5 wt. %, about 6.0 wt. %, about 6.5 wt. %, about 7.0 wt. %, about 7.5 wt. %, about 8.0 wt. %, about 8.5 wt. %, about 9.0 wt. %, about 9.5 wt. %, or about 10.0 wt. %.

The amount of aqueous composition injected into the subterranean reservoir can and will vary depending, for example, on the properties of the subterranean formation (e.g., temperature, salinity, size, geology, etc.).

In some embodiments, the amount of aqueous composition injected into the subterranean formation may be from about 10 barrels (bbls) to about 5,000 bbls. In other embodiments, the amount of aqueous composition injected into the subterranean formation may be about 10 bbls, about 20 bbls, about 30 bbls, about 40 bbls, about 50 bbls, about 60 bbls, about 70 bbls, about 80 bbls, about 90 bbls, about 100 bbls, about 150 bbls, about 200 bbls, about 250 bbls, about 300 bbls, about 350 bbls, about 400 bbls, about 450 bbls, about 500 bbls, about 550 bbls, about 600 bbls, about 650 bbls, about 700 bbls, about 750 bbls, about 800 bbls, about 850 bbls, about 900 bbls, about 950 bbls, about 1,000 bbls, about 1,250 bbls, about 1,500 bbls, about 1,750 bbls, about 2,000 bbls, about 2,250 bbls, about 2,500 bbls, about 2,750 bbls, about 3,000 bbls, about 3,250 bbls, about 3,500 bbls, about 3,750 bbls, about 4,000 bbls, about 4,250 bbls, about 4,500 bbls, about 4,750 bbls, or about 5,000 bbls.

(iii) Shut-In Period

The SWCTT comprises subjecting the subterranean reservoir to a shut-in period following injection of the at least three chemically reactive tracers to allow said chemically reactive tracers to move through the subterranean reservoir and undergoes hydrolysis, thereby producing the corresponding product tracers (i.e., the corresponding alcohol of the injected ester tracer).

In an embodiment, the shut-in period may be from about 0.5 day to about 7 days. In some embodiments, the shut-in period may be about 0.5 day, about 1 day, about 1.5 days, about 2 days, about 2.5 days, about 3 days, about 3.5 days, about 4 days, about 4.5 days, about 5 days, about 5.5 days, about 6 days, about 6.5 days, or about 7 days. In a preferred embodiment, the shut-in period may be about 2.5 days.

In some embodiments, a first single well chemical tracer test is conducted, followed by a shut-in period, and then a second single well chemical tracer test is conducted, followed by second another shut-in period. In other embodiments, a first single well chemical tracer test is conducted, and then a second single well chemical tracer test is conducted, followed by another shut-in period.

(iv) Sampling

The SWCTT comprises sampling a produced fluid and determining the concentration of the at least three chemically reactive tracers and the concentrations of the corresponding product tracers in the produced fluid after a shut-in period.

The SWCTT comprises sampling a produced fluid after the shut-in period. In some embodiments, the well is produced to bring a produced fluid to the surface. The produced fluid comprises the at least three chemically reactive tracers and the corresponding product tracers.

In some embodiments, the well is produced at a rate of about 100 bbls/day to about 1,000 bbls/day. In other embodiments, the well is produced at a rate of about 100 bbls/day, about 150 bbls/day, about 200 bbls/day, about 250 bbls/day, about 300 bbls/day, about 350 bbls/day, about 400 bbls/day, about 450 bbls/day, about 500 bbls/day, about 550 bbls/day, about 600 bbls/day, about 650 bbls/day, about 700 bbls/day, about 750 bbls/day, about 800 bbls/day, about 850 bbls/day, about 900 bbls/day, about 950 bbls/day, or about 1,000 bbls/day.

The SWCTT comprises sampling the at least three chemically reactive tracers and the corresponding product tracers produced after the shut-in period. In some embodiments, samples of the produced fluid are obtained at intervals of about 5 to about 30 minute. In some embodiments, samples of the produced fluid are obtained at intervals of 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or 30 minutes.

The SWCTT comprises determining the concentrations of the chemically reactive tracers and the concentrations of the corresponding product tracers in the produced water. In some embodiments, determining the concentrations of the chemically reactive tracers and the corresponding product tracers in the produced water may be carried out by a chromatographic method. In some embodiments, the chromatographic method may be gas chromatography or liquid chromatography. In preferred embodiments, the chromatographic method may be gas chromatography.

(v) Determining an $S_{OR}$ Value

The SWCTT comprises determining a residual oil saturation ($S_{OR}$) of the subterranean reservoir. In some embodiments, the concentrations of the at least three chemically reactive tracers (i.e., esters) and the concentrations of the at least three product tracers (i.e., alcohols) in the produced water are plotted against the volume of the produced water. In some embodiments, the residual oil saturation is calculated using the following formulas:

$$\beta = \frac{Qa - WBV}{Qb - WBV}$$

Wherein $\beta$=the retardation factor of the ester,
Qa=the mid-point volume of the ester,
Qb=the mid-point volume of the alcohol, and
WBV=well-bore volume.

$$S_{OR} = \frac{\beta}{\beta + Ki}$$

Wherein $S_{OR}$=residual oil saturation;
$\beta$=the retardation factor of the ester; and
Ki=the partitioning coefficient (as determined experimentally in a lab setting).

(vi) Saturation Profile

The SWCTT comprises determining a saturation profile of the subterranean reservoir. In some embodiments, a saturation profile may be obtained by plotting the $S_{OR}$ value obtained from at least three chemically reactive tracers against a chemically reactive tracer contact volume to yield a saturation profile of the subterranean reservoir. In some embodiments, the saturation profile graph may comprise from three to ten $S_{OR}$ values. In other embodiments, the saturation profile may comprise three $S_{OR}$ values, four $S_{OR}$ values, five $S_{OR}$ values, six $S_{OR}$ values, seven $S_{OR}$ values, eight $S_{OR}$ values, nine $S_{OR}$ values, or ten $S_{OR}$ values.

(c) Using Straight Line Analysis

An additional aspect of the present disclosure encompasses performing a straight line analysis on a saturation profile of a subterranean reservoir.

In general, a straight line analysis is performed on the saturation profile. As the injected surfactant mass is known, the key is to derive the surfactant contact volume or the pore volume that surfactant was effective in displacing oil from the measured saturation profile. In some embodiments, the intercept from the straight line drawn on the oil saturation profile indicates the effective surfactant contact volume. In some embodiments, the straight lines are drawn using two points on each saturation profile. In some embodiments, the surfactant effective contact pore volume is read from the intercept to the x-axis.

In other embodiments, the oil saturation profile from the SWCTT test exhibits a straight line at the transition zone (from surfactant effective region to the untouched reservoir volume by surfactant). In further embodiments, the intercept of the straight line on the tracer contact volume axis gives the effective surfactant contact volume. As the injected surfactant mass is known, the surfactant retention is the ratio of the surfactant injection mass divided by the effective surfactant contact reservoir volume.

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

The term "subterranean reservoir," as used herein may include a subsurface rock or sand formation from which a production fluid, or resource, can be harvested. The formation may include sand, granite, silica, carbonates, clays, and organic matter, such as heavy oil (e.g., bitumen), oil, gas, or coal, among others. Reservoirs may vary in thickness from less than one foot (0.3 meters) to hundreds of feet (hundreds of meters). The resource is generally a hydrocarbon, such as oil.

The term "subterranean," as used herein refers to locations below the surface of the Earth.

The term "surface," as used herein refers to locations at or above the surface of the Earth, ice, ocean bottom, river bottom, lake bottom, and/or body of water, such as a lake, river, or ocean.

The term "product tracer," as used herein refers to a chemically reactive ester that is hydrolyzed to form the corresponding alcohol.

As various changes could be made in the above-described methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following abbreviation used herein: EACN=equivalent alkane carbon number.

Example 1

Single Well Chemical Tracer Test

A single well chemical tracer test is simulated at field test site in the United States. The single well chemical tracer test is conducted by injecting a total of six chemically reactive tracers. A total of six chemically reactive tracers (Table 1) are into the injection well at the test site.

TABLE 1

Chemically Reactive Tracers

| Tracer | Identity |
|---|---|
| A | Ethyl formate |
| B | N-propyl formate |
| C | Methyl acetate |
| D | Ethyl acetate |
| E | Iso-propyl acetate |
| F | t-butyl acetate |

The chemically reactive tracers are pumped into the injection well together: A, B, C, D, E, and F.

After injection of the chemically reactive tracers, the reservoir is shut-in for a period of time. Following the shut-in period, the injection well is produced. Samples are taken from the produced water and analyzed with gas chromatography.

Residual oil saturations ($S_{OR}$) are calculated for Tracer A, B, C, D, E, and F by plotting the concentration of the product tracers vs. production volume.

An oil saturation profile for the subterranean reservoir is obtained by plotting the average oil saturation for each chemically reactive tracer vs. tracer contact volume (FIG. 1A).

Figure 1B:
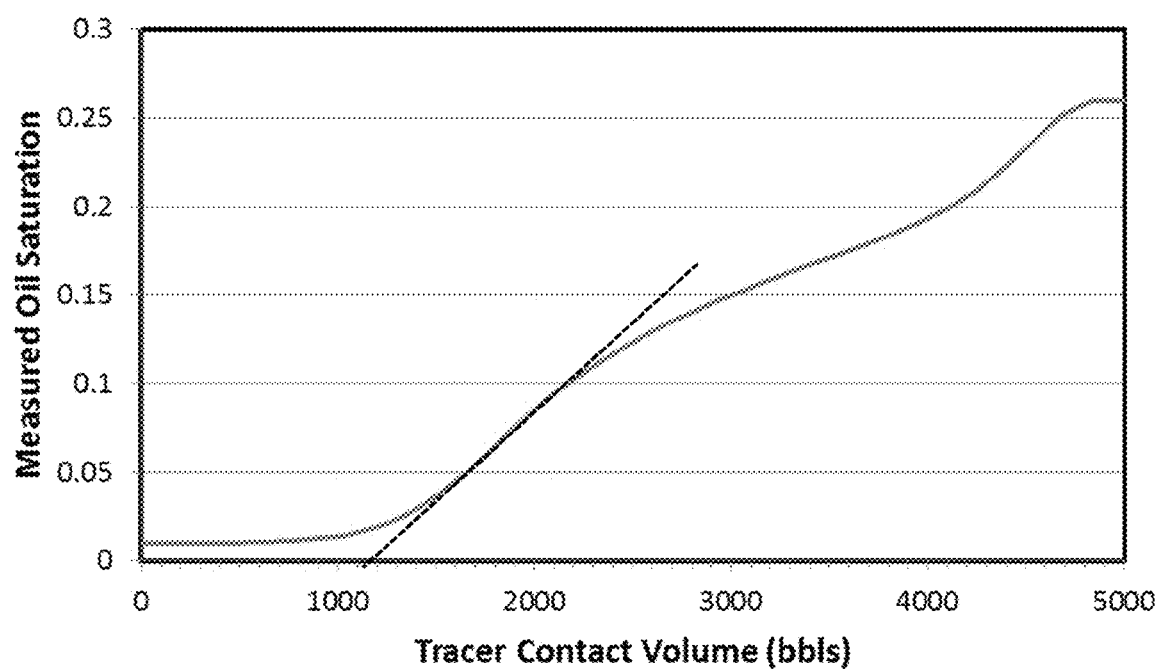
FIG. 1B depicts a graph of measured oil saturation vs. tracer contact volume (bbls) with a dotted line drawn through two oil saturation points.
Figure 1C:
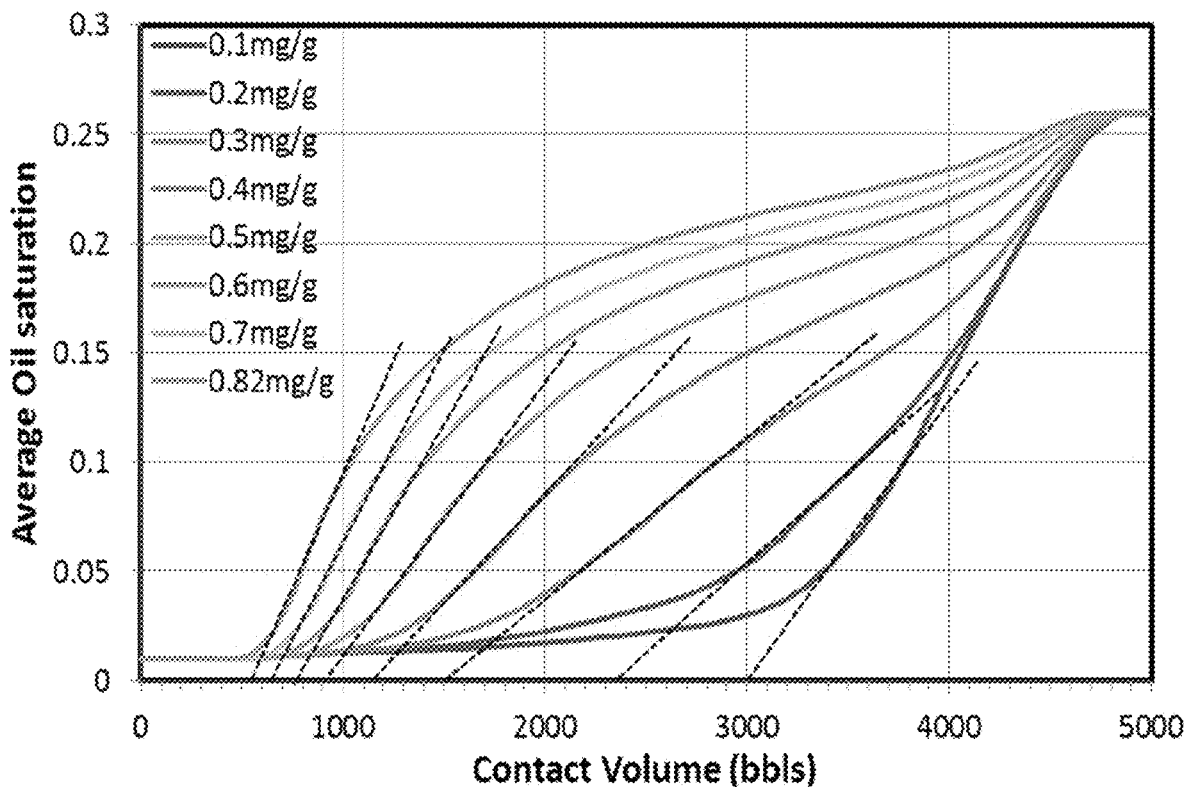
FIG. 1C depicts a graph of average oil saturation vs. contact volume (bbls) with dotted lines drawn using two points (average oil saturation at 0.05 and 0.1) on each saturation profile.
Figure 1D:
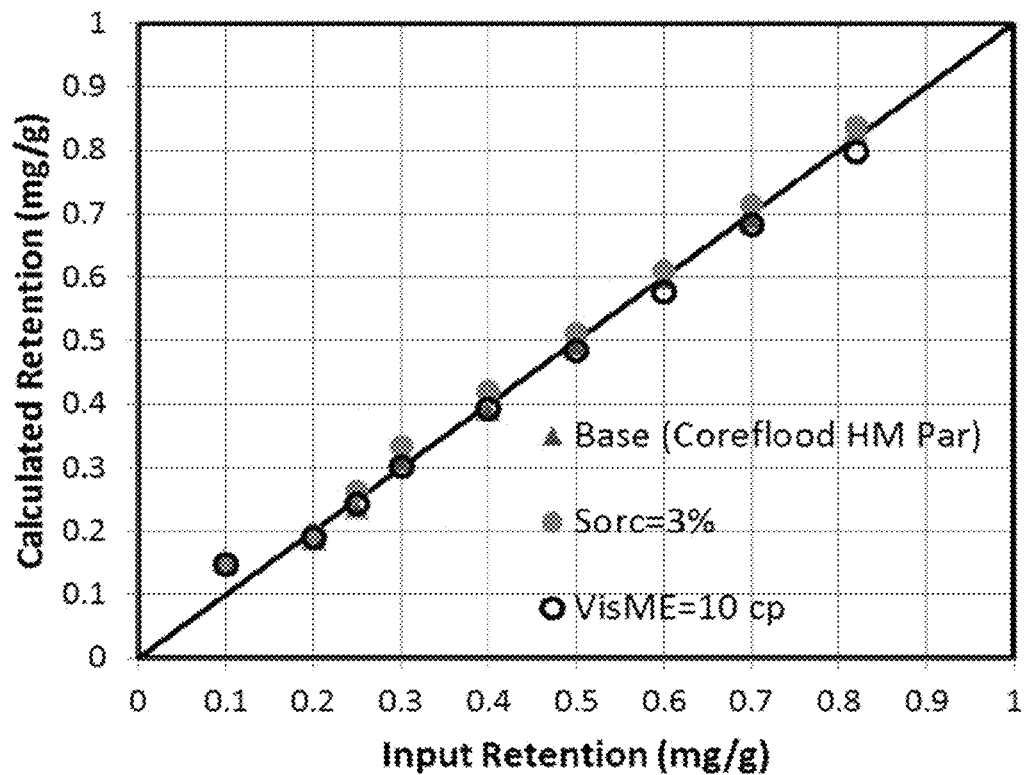
FIG. 1D depicts a graph of calculated retention (mg/g) vs. input retention (mg/g).

A straight line analysis is performed on the saturation profile (FIG. 1B). As the injected surfactant mass is known, the key is to derive the surfactant contact volume or the pore volume that surfactant was effective in displacing oil from the measured saturation profile. For the simulated saturation profile shown in FIG. 1A, the simulation input surfactant retention is 0.4 mg/g with a contact pore volume of 1180 bbls. Inspecting the oil saturation profile for this case (FIG. 1B) indicates this contact volume corresponds to the intercept from the straight line drawn in the ASP effective zone (FIG. 1A). This observation is applied to the saturation profiles of different surfactant retention in FIG. 1C. The straight lines are drawn using two points (average oil saturation at 0.05 and 0.1) on each saturation profile. The surfactant effective contact pore volume is read from the intercept to the x-axis. The calculated surfactant retention using this contact volume is plotted against input surfactant retention of FIG. 1D (triangles). There is good agreement between the calculated surfactant retention and input surfactant retention to the simulator. Changing simulation conditions (e.g., $S_{orc}$ and micro-emulsion viscosity) did not affect the accuracy of the calculated surfactant retention.

Figure 1E:
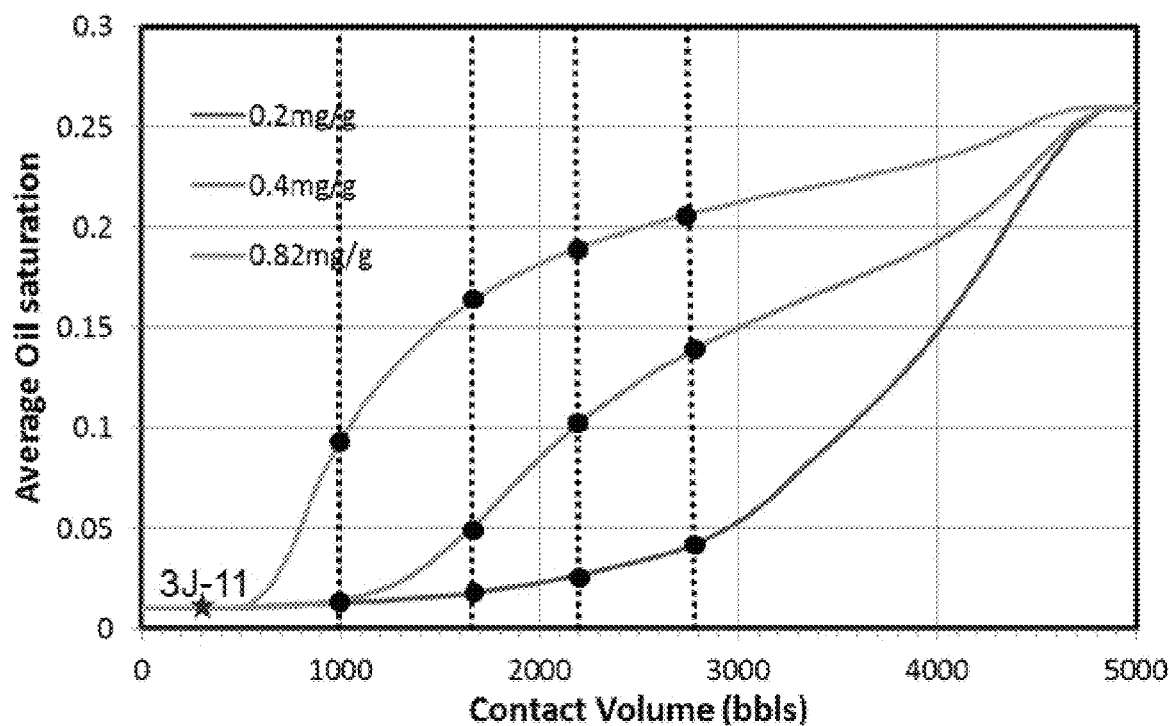
FIG. 1E depicts a graph of average oil saturation vs. contact volume (bbls) with vertical dotted lines drawn through the saturation points to define the surfactant contact volume.

In the above surfactant retention calculation, it is assumed that a smooth oil saturation profile is available. However, this is not the case for the saturation profile obtained from the field SWCTT, which only provides 4 or 5 saturation points of this curve as illustrated in FIG. 1A. A successful SWCTT design for surfactant retention quantification needs to have the following two characteristics within the uncertainty of the expected surfactant retention range: 1) at least one saturation point measures the residual oil saturation $S_{orc}$; 2) at least two saturation points lands within the transition zone from $S_{orc}$ to $S_{orw}$ on the saturation profile so that a straight line can be drawn through them to define the surfactant contact volume. Such a design is illustrated in FIG. 1E, where the target surfactant retention is 0.4 mg/g. The first saturation point measures $S_{orc}$ for the target surfactant retention. The next two saturation points are located in the transition zone and can be used to draw the straight line for contact volume determination. If the actual surfactant retention is higher than the target surfactant retention in the design, for example the actual surfactant retention is 0.82 mg/g, most of the saturation points will land in the region beyond the transition zone. In this case, the test will not be able to define $S_{orc}$ and surfactant retention quantitatively. However, one may only conclude that the surfactant retention is higher than design target. On the other hand, if the actual surfactant retention is much lower (e.g., 0.2 mg/g) than the target value 0.4 mg/g, it is possible that all saturation points measure $S_{orc}$ and leaves no saturation points in the transition zone to define the surfactant retention. In this case, one may only know that the actual surfactant retention is lower but not the quantitative value.

Figure 1F:
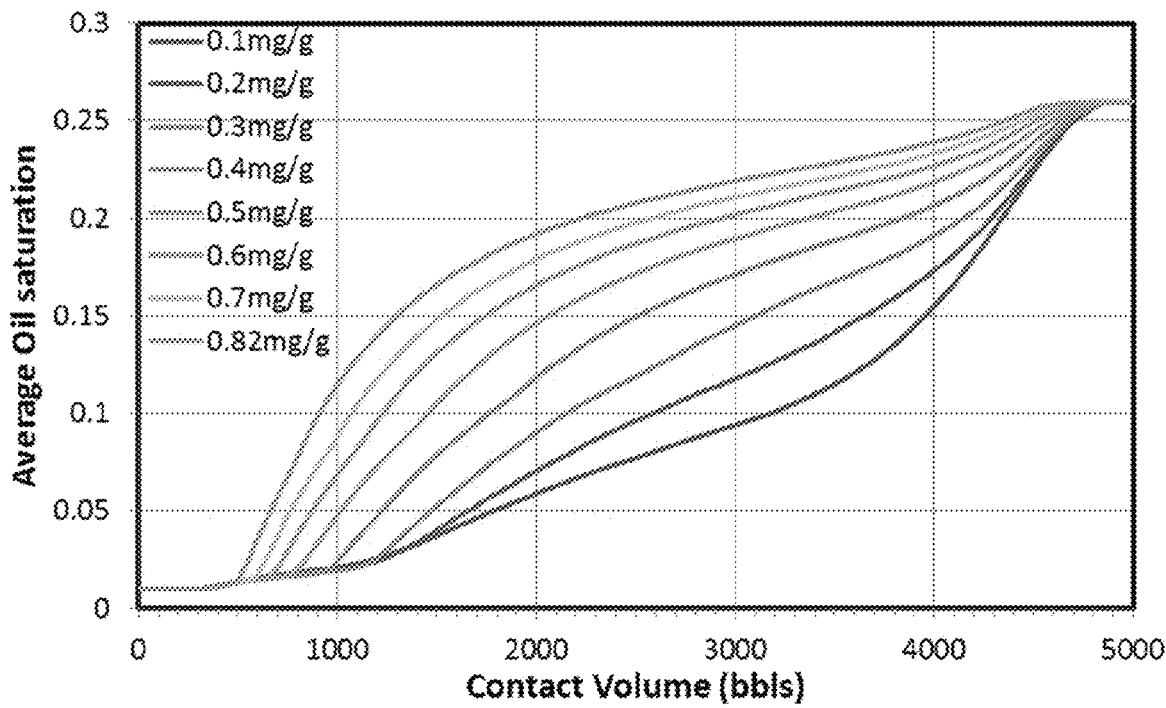
FIG. 1F depicts a graph of average oil saturation vs. contact volume (bbls) for a low solubilization ratio.
Figure 1G:
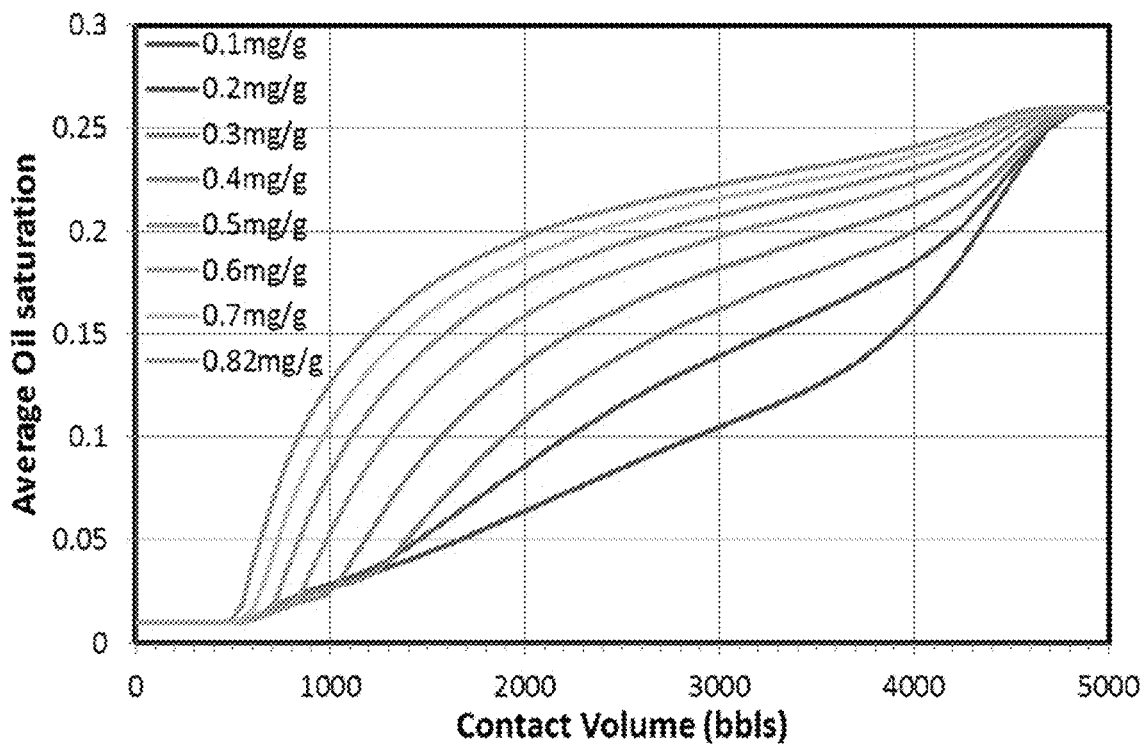
FIG. 1G depicts a graph of average oil saturation vs. contact volume (bbls) for an unfavorable capillary desaturation curve (CDC).
Figure 1H:
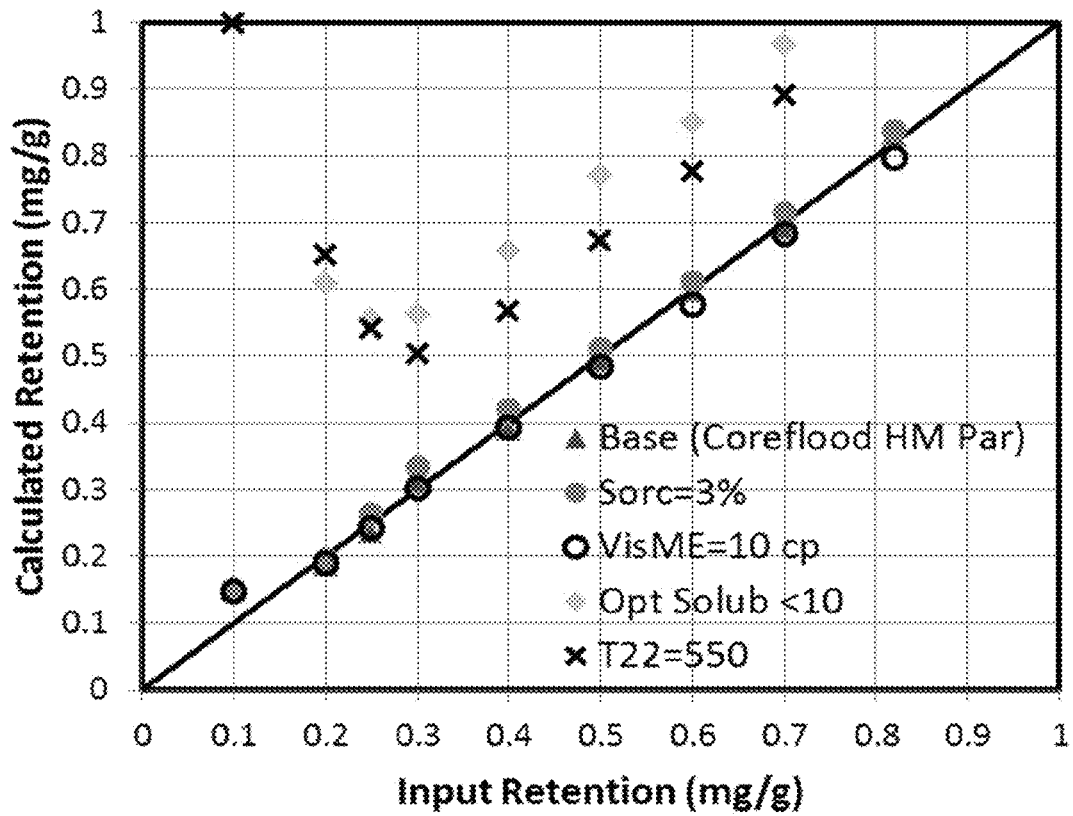
FIG. 1H depicts a graph of calculated retention (mg/g) vs. input retention (mg/g).

In the above discussion, an effective chemical formulation is assumed and the chemical slug is able to displace oil effectively as long as there is sufficient surfactant. If chemical formation is not able to achieve ultra-low IFT due to low surfactant solubilization ratio or unfavorable capillary desaturation curve (CDC), the characteristics of the saturation profile are not only affected by surfactant retention, but also the effectiveness of the formulation as shown in FIG. 1F and FIG. 1G. In either case, the calculated surfactant retention is much higher than the actual value as shown in FIG. 1H. The low surfactant retention cases are affected more than the high retention cases.

What is claimed is:

1. A method for determining a surfactant retention value in a subterranean reservoir comprising one or more injected surfactants, the method comprising:
   providing the one or more injected surfactants in the subterranean reservoir;
   generating a saturation profile using a first single well chemical tracer test and a second single well chemical tracer test, wherein the first single well chemical tracer test includes injecting into the subterranean reservoir, at a well, at least three chemically reactive tracers as a first volume of chemically reactive tracers, and the second single well chemical tracer test includes injecting into the subterranean reservoir, at the well and following a first shut-in period for the first single well tracer test, the at least three chemically reactive tracers as a second volume of chemically reactive tracers that is greater than the first volume, the saturation profile being based on:
      producing a first sample of a fluid from the subterranean reservoir after the first single well chemical tracer test and a second sample of the fluid after the second single well chemical tracer test;
      measuring a concentration of the at least three chemically reactive tracers in the first sample of the fluid and the second sample of the fluid;
      measuring a concentration of a product tracer, corresponding to the at least three chemically reactive tracers, in the first sample of the fluid and in the second sample of the fluid;
      determining a plurality of residual oil saturation values based on the concentration of the at least three chemically reactive tracers and the concentration of the product tracer; and
      plotting the plurality of residual oil saturation values against a chemically reactive tracer contact volume; and
   conducting a straight line analysis on the saturation profile to determine the surfactant retention value.

2. The method of claim 1, wherein after the second volume of chemically reactive tracers is injected into the subterranean reservoir a slug of brine is injected into the subterranean reservoir.

3. The method of claim 1, wherein the at least three chemically reactive tracers are selected from the group consisting of methyl formate, ethyl formate, propyl formate, N-propyl formate, isobutyl formate, t-butyl formate, methyl acetate, ethyl acetate, propyl acetate, isopropyl acetate, t-butyl acetate, ethyl acetoacetate, ethylene glycol monomethyl ether acetate, ethylene glycol monethyl ether acetate, ethylene glycol monobutyl ether acetate, and combinations thereof.

4. The method of claim 3, wherein the at least three chemically reactive tracers are selected from the group consisting of methyl acetate, ethyl acetate, isopropyl acetate, t-butyl acetate, propyl formate, ethyl formate, and combinations thereof.

5. The method of claim 1, wherein the at least three chemically reactive tracers are present in an aqueous composition in an amount from about 0.1 wt. % to about 10 wt. %.

6. The method of claim 1, wherein generating the saturation profile comprises subjecting the subterranean reservoir to the first shut-in period being about 1 day to about 4 days.

7. The method of claim 6, wherein the shut-in period is for about 2.5 days.

8. The method of claim 1, wherein the produced fluid includes the at least three chemically reactive tracers and at least three product tracers.

9. The method of claim 8, wherein the produced fluid is sampled to determine concentrations of the at least three chemically reactive tracers and concentrations of the at least three product tracers.

10. The method of claim 1, wherein a surfactant contact volume is used with the straight line analysis to determine the surfactant retention value.

11. The method of claim 1, wherein a ratio of the first volume to the second volume is between 1:1 and 1:5.

12. The method of claim 1, wherein conducting the straight line analysis on the saturation profile includes determining an x-axis intercept of the saturation profile.

13. The method of claim 12, wherein determining the surfactant retention value includes dividing an injection mass of the one or more injected surfactants by an effective surfactant contact reservoir volume indicated by the x-axis intercept.

14. The method of claim 1, wherein generating the saturation profile includes plotting between three and ten values of the plurality of residual oil saturation values.

15. A method for determining a surfactant retention value in a subterranean reservoir including one or more injected surfactants, the method comprising:
   performing a first single well chemical tracer test that includes injecting at least three chemically reactive tracers as a first volume of chemically reactive tracers into the subterranean reservoir at a well followed by a first shut-in period;
   performing a second single well chemical tracer test that includes injecting a second volume of the at least three chemically reactive tracers that is greater than the first volume into the subterranean reservoir at the well followed by a second shut-in period;
   producing a first sample of fluid from the subterranean reservoir after performing the first single well chemical tracer test and a second sample of fluid after performing the second single well tracer test;
   generating a saturation by:
      measuring a concentration of the at least three chemically reactive tracers in the first sample of the fluid and the second sample of the fluid;
      measuring a concentration of a product tracer, corresponding to the at least three chemically reactive tracers, in the first sample of the fluid and in the second sample of the fluid;
      determining a plurality of residual oil saturation values based on the concentration of the at least three chemically reactive tracers and the concentration of the product tracer; and
      plotting the plurality of residual oil saturation values against a chemically reactive tracer contact volume;
   conducting a straight line analysis on the saturation profile; and
   determining a surfactant retention value based at least partly on the straight line analysis.

16. The method of claim 15, wherein conducting the straight line analysis includes determining an x-axis intercept of the saturation profile that indicates an effective surfactant contact reservoir volume, and determining the surfactant retention value includes dividing an injection mass of the one or more injected surfactants by the effective surfactant contact volume.

\* \* \* \* \*